(12) United States Patent
Narimatsu et al.

(10) Patent No.: US 6,758,820 B2
(45) Date of Patent: Jul. 6, 2004

(54) ARTERIAL-PULSE-WAVE DETECTING APPARATUS

(75) Inventors: Kiyoyuki Narimatsu, Komaki (JP); Toshihiko Ogura, Komaki (JP)

(73) Assignee: Colin Medical Technology Corporation, Komaki (JP)

(*) Notice: Subject to any disclaimer, the term of this patent is extended or adjusted under 35 U.S.C. 154(b) by 106 days.

(21) Appl. No.: 10/265,396

(22) Filed: Oct. 7, 2002

(65) Prior Publication Data

US 2003/0158488 A1 Aug. 21, 2003

(30) Foreign Application Priority Data

Feb. 21, 2002 (JP) ........................................ 2002-044894

(51) Int. Cl.[7] .............................................. A61O 5/02
(52) U.S. Cl. ...................................... 600/492; 600/490
(58) Field of Search ................................ 600/481, 485, 600/490, 492, 493, 494, 495, 496, 500, 501, 502, 503

(56) References Cited

U.S. PATENT DOCUMENTS 6,332,869 B1 * 12/2001 Ogura et al. ................ 600/490
6,338,718 B1 * 1/2002 Ogura ......................... 600/490
6,379,309 B1 * 4/2002 Ogura et al. ................ 600/490

FOREIGN PATENT DOCUMENTS

| EP | 0 835 633 A2 | 4/1998 |
| EP | 1 053 714 A2 | 11/2000 |

* cited by examiner

Primary Examiner—Mary Beth Jones
Assistant Examiner—Navin Natnithithadha
(74) Attorney, Agent, or Firm—Oliff & Berridge, PLC

(57) ABSTRACT

An arterial-pulse-wave detecting apparatus, including a plurality of pulse-wave detecting devices which are adapted to be worn on a plurality of portions of a living subject, respectively, and detect respective pulse waves that are produced in synchronism with each other from respective arteries of the plurality of portions of the subject, a memory device which stores the respective pulse waves produced in synchronism with each other and detected by the plurality of pulse-wave detecting devices, and a pulse-wave-display control device for controlling a display device to display the respective pulse waves produced in synchronism with each other and stored by the memory device, such that the respective pulse waves are superposed on each other.

9 Claims, 8 Drawing Sheets

FIG. 6

| FIRST ARTERY | SECOND ARTERY | THIRD ARTERY | FOURTH ARTERY | STENOTIC PORTION |
|---|---|---|---|---|
| ○ | ○ | ○ | ○ | NONE |
| ○ | × | ○ | ○ | F |
| × | ○ | ○ | ○ | E |
| ○ | ○ | ○ | × | C |
| ○ | ○ | × | ○ | B |
| × | × | ○ | ○ | D |
| × | × | × | × | A |

○ : ABSENCE OF STENOSIS

× : PRESENCE OF STENOSIS

ARTERIAL-PULSE-WAVE DETECTING APPARATUS

BACKGROUND OF THE INVENTION

1. Field of the Invention

The present invention relates to an arterial-pulse-wave detecting apparatus which detects respective pulse waves produced from respective arteries of a plurality of portions of a living subject.

2. Related Art Statement

Since a pulse wave which is produced from an artery of a living subject includes various sorts of information related to the circulatory organ of the subject, the pulse wave is analyzed to make a diagnosis or judgment about arteriosclerosis, arteriostenosis, peripheral circulation, etc. However, since it is considerably difficult to identify a small change of shape or form of a portion of the pulse wave, a person may have failed to identify circulatory-organ-related information corresponding to the change of the waveform.

In the above-indicated background, it is possible to provide an arterial-pulse-wave detecting apparatus which detects respective pulse waves produced from respective arteries of a plurality of portions of a living subject, e.g., left and right portions located at respective positions symmetrical with each other with respect to a median line of the subject (because the circulatory organ is substantially symmetrical with respect to the median line), and which operates a display device to simultaneously display those pulse waves. However, if those pulse waves are displayed in a separated manner, it is yet difficult to identify a small change corresponding to an initial symptom of a disease, and accordingly a person such as a doctor may disadvantageously make a judgment influenced by his or her subjective factors.

SUMMARY OF THE INVENTION

It is therefore an object of the present invention to provide an arterial-pulse-wave detecting apparatus which detects respective pulse waves produced from respective arteries of a plurality of portions of a living subject and which allows a person to, or can itself, make an accurate judgment about a change or a difference of a form or respective forms of one or more of the respective pulse waves detected.

The above object has been achieved by the present invention. According to the present invention, there is provided an arterial-pulse-wave detecting apparatus, comprising a plurality of pulse-wave detecting devices which are adapted to be worn on a plurality of portions of a living subject, respectively, and detect respective pulse waves that are produced in synchronism with each other from respective arteries of the plurality of portions of the subject; a memory device which stores the respective pulse waves produced in synchronism with each other and detected by the plurality of pulse-wave detecting devices; and a pulse-wave-display control means for controlling a display device to display the respective pulse waves produced in synchronism with each other and stored by the memory device, such that the respective pulse waves are superposed on each other.

According to this invention, the pulse-wave-display control means controls the display device to display the respective pulse waves produced in synchronism with each other, detected by the plurality of pulse-wave detecting devices, and stored by the memory device, such that the respective pulse waves are superposed on each other. Thus, each one of those waveforms can be easily compared with the other waveform or waveforms. Therefore, a person such as a doctor can easily and accurately identify a small change of any one of those waveforms. Thus, the accuracy of inspection of the waveform of each arterial pulse wave is improved.

According to a preferred feature of the present invention, the pulse-wave-display control means controls the display device to display the respective pulse waves produced in synchronism with each other, such that respective minimal points of the respective pulse waves coincide with each other.

According to this feature, the respective pulse waves produced in synchronism with each other, are displayed such that respective minimal points of the respective pulse waves coincide with each other. Thus, a person can more easily and accurately identify a small change or difference of the waveform of any of the arterial pulse waves.

According to another feature of the present invention, the pulse-wave-display control means controls the display device to display the respective pulse waves produced in synchronism with each other, such that respective rising points of the respective pulse waves coincide with each other.

According to this feature, the respective pulse waves produced in synchronism with each other, are displayed such that respective rising points of the respective pulse waves coincide with each other. Thus, a person can more easily and accurately identify a small change of the waveform of any of the arterial pulse waves.

According to another feature of the present invention, wherein the pulse-wave-display control means controls the display device to display the respective pulse waves produced in synchronism with each other, such that respective amplitudes of the respective pulse waves are equal to each other.

According to this feature, the respective pulse waves produced in synchronism with each other, are displayed such that respective amplitudes of the respective pulse waves are equal to each other. Thus, a person can more easily and accurately identify a small change of the waveform of any of the arterial pulse waves.

According to another feature of the present invention, the apparatus further comprises an area-difference determining means for determining a difference between respective areas of the respective pulse waves displayed on the display device by the pulse-wave-display control means such that the respective pulse waves are superposed on each other, wherein the pulse-wave-display control means controls the display device to display the difference determined by the area-difference determining means.

According to this feature, the difference of respective areas of the respective pulse waves superposed on each other, determined by the area-difference determining means, is displayed on the display device. Thus, the difference of the two waveforms is quantitatively determined. In addition, a slow or overall change of a waveform that cannot be easily recognized in a conventional manner, can be easily identified according to this feature.

According to another feature of the present invention, the plurality of pulse-wave detecting devices comprise two pulse-wave-detecting devices which include respective portions adapted to be worn on left and right portions of the subject, respectively, that are located at respective positions symmetrical with each other with respect to a median line of the subject, and detect the respective pulse waves produced from the respective arteries of the left and right portions of the subject, and wherein the pulse-wave-display control means controls the display device to display the respective pulse waves produced from the respective arteries of the left and right portions of the subject, such that the respective pulse waves are superposed on each other.

According to this feature, the plurality of pulse-wave detecting devices detect the respective pulse waves produced in synchronism with each other from the left and right portions of the subject that are located at the respective positions symmetrical with each other with respect to the median line of the subject, the memory device stores the two pulse waves, and the pulse-wave-display control means operates the display device to display the two pulse waves such that those pulse waves are superposed on each other. Thus, a person can more easily compare the two pulse waves with each other and accordingly can more easily and accurately identify even a small change of either one of the two waveforms. That is, the accuracy of inspection of waveform of each arterial pulse wave can be improved. Since the two waveforms should be basically identical with each other, the change of each of the waveforms can be more easily identified.

BRIEF DESCRIPTION OF THE DRAWINGS

The above and optional objects, features, and advantages of the present invention will be better understood by reading the following detailed description of the preferred embodiments of the invention when considered in conjunction with the drawings, in which:

FIG. 6 is a table representing a pre-stored relationship that is used to identify an arteriostenotic portion of the subject;

DETAILED DESCRIPTION OF PREFERRED EMBODIMENTS

Figure 1:
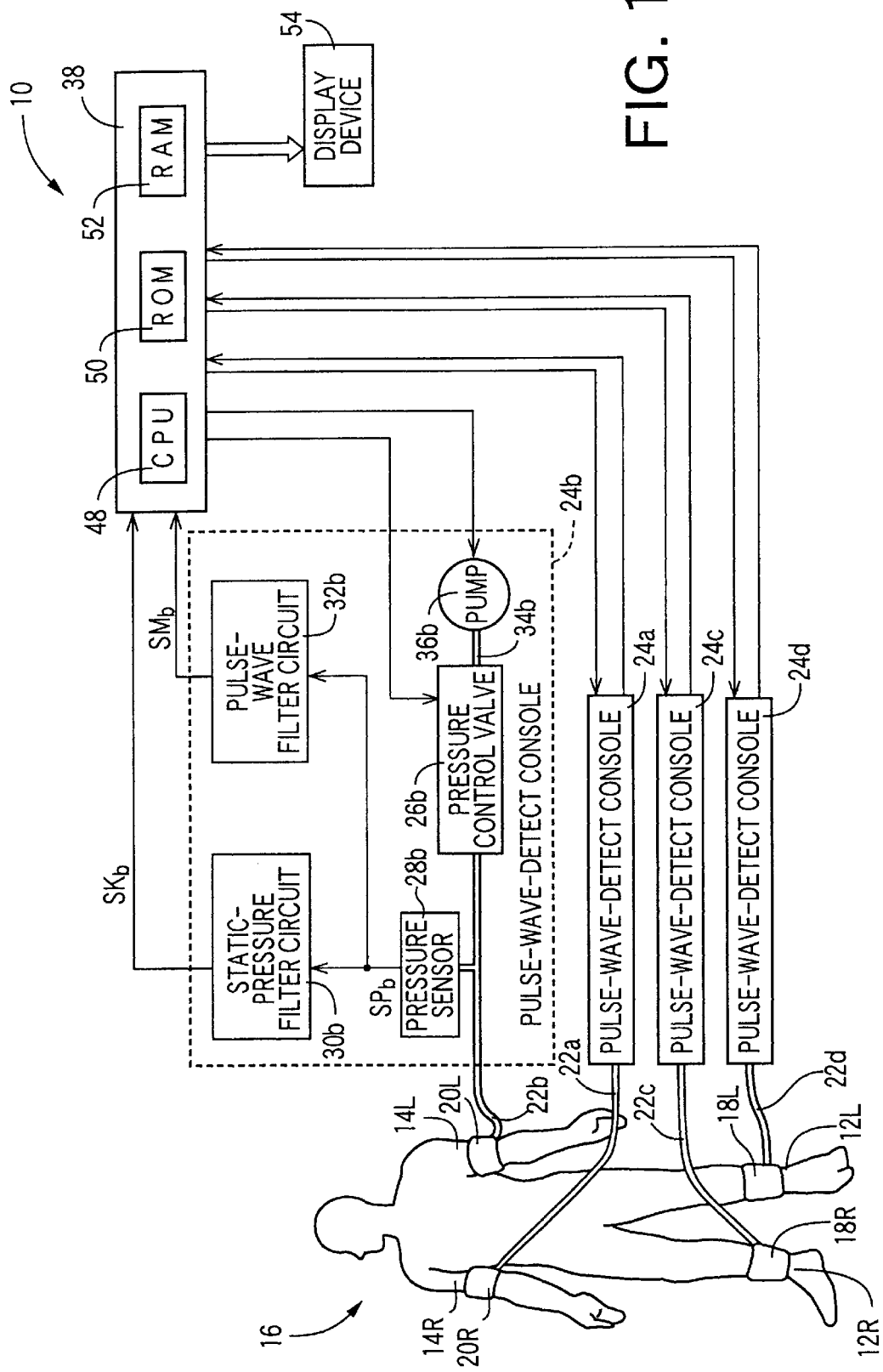
FIG. 1 is a diagrammatic view for explaining a construction of an arterial-pulse-wave detecting apparatus to which the present invention is applied.

Hereinafter, there will be described in detail an embodiment of the present invention by reference to the drawings. FIG. 1 shows a diagrammatic view for explaining a construction of an arterial-pulse-wave detecting apparatus 10 to which the present invention is applied.

In FIG. 1, the arterial-pulse-wave detecting apparatus 10 includes a left ankle cuff 18L and a right ankle cuff 18R which are wound around a left ankle 12L and a right ankle 12R, respectively, of a patient 16, and a left upper-arm cuff 20L and a right upper-arm cuff 20R which are wound around a left upper arm 14L and a right upper arm 14R, respectively, of the patient 16. Each of the cuffs 18L, 18R, 20L, 20R functions as a pressing band which presses a portion of the patient around which the each cuff is wound, and includes a belt-like outer bag which is formed of a non-stretchable material such as cloth or polyester; and a rubber bag accommodated in the outer bag.

The left and right upper-arm cuffs 20L, 20R are connected via respective pipings 22b, 22a to respective pulse-wave-detect consoles 24b, 24a; and the left and right ankle cuffs 18L, 18R are connected via respective pipings 22d, 22c to respective pulse-wave-detect consoles 24d, 24c.

Since the four pulse-wave-detect consoles 24a, 24b, 24c, 24d have an identical construction with one another, the pulse-wave-detect console 24b to which the left upper-arm cuff 20L is connected will be described below as a representative of the four devices 24. The pulse-wave-detect console 24b includes a pressure control valve 26b, a pressure sensor 28b, a static-pressure filter circuit 30b, a pulse-wave filter circuit 32b, a piping 34b, and an air pump 36b, and the piping 22b is connected to the pressure control valve 26b and the pressure sensor 28b. The pressure control valve 26b is connected via the piping 34b to the air pump 36b.

The pressure control valve 26b controls a pressure of a pressurized air supplied from the air pump 36b, supplies the pressure-controlled air to the left upper-arm cuff 20L, and discharges the pressurized air from the left upper-arm cuff 20L, so as to control the air pressure in the cuff 20L.

The pressure sensor 28b detects the air pressure in the left upper-arm cuff 20L, and supplies a pressure signal, $SP_b$, representing the detected air pressure, to the static-pressure filter circuit 30b and the pulse-wave filter circuit 32b. The static-pressure filter circuit 30b includes a low-pass filter which extracts, from the pressure signal $SP_b$, a cuff-pressure signal, $SK_b$, representing a static component of the detected pressure, i.e., a pressing pressure of the cuff 20L (hereinafter, referred to as the left-upper-arm cuff pressure, $PC_b$). The filter circuit 30b supplies the cuff-pressure signal $SK_b$ to an electronic control device 38 via an A/D (analog-to-digital) converter, not shown.

The pulse-wave filter circuit 32b includes a band-pass filter which extracts, from the pressure signal $SP_b$, a left-upper-arm pulse-wave signal, $SM_b$, representing a left-upper-arm pulse wave $WB_L$ as an oscillatory component of the detected pressure that has prescribed frequencies. The filter circuit 32b supplies the pulse-wave signal $SM_b$ to the control device 38 via an A/D converter, not shown. Since the pulse-wave signal $SM_b$ represents the left-upper-arm pulse wave $WB_L$ produced from an artery of the left upper arm 14L pressed by the left upper-arm cuff 20L, the left upper-arm cuff 20L and the pulse-wave-detect console 24b cooperate with each other to function as a left-upper-arm-pulse-wave detecting device 40 (FIG. 2).

Similarly, a right-upper-arm pulse wave $WB_R$ is represented by a right-upper-arm pulse-wave signal $SM_a$ extracted by a pulse-wave filter circuit 32a, and accordingly the right upper-arm cuff 20R and the pulse-wave-detect console 24a cooperate with each other to function as a right-upper-arm-pulse-wave detecting device 42. Moreover, a left-ankle pulse wave $WA_L$ is represented by a left-ankle pulse-wave signal $SM_d$ extracted by a pulse-wave filter circuit 32d, and accordingly the left ankle cuff 18L and the pulse-wave-detect console 24d cooperate with each other to function as a left-ankle-pulse-wave detecting device 44. Similarly, a right-ankle pulse wave $WA_R$ is represented by a right-ankle pulse-wave signal $SM_c$ extracted by a pulse-wave filter circuit 32c, and accordingly the right ankle cuff 18R and the pulse-wave-detect console 24c cooperate with each other to function as a right-ankle-pulse-wave detecting device 46. Two pulse waves arbitrarily selected from the left-upper-arm pulse wave $WB_L$, the right-upper-arm pulse wave $WB_R$, the left-ankle pulse wave $WA_L$, and the right-ankle pulse wave $WA_R$ function as a first pulse wave and a second pulse wave, respectively; and two pulse-wave detecting devices out of the four devices 40, 42, 44, 46 that detect the first and second pulse waves, respectively, function as a first-pulse-wave detecting device and a second-pulse-wave detecting device, respectively.

The control device 38 is essentially provided by a microcomputer including a CPU (central processing unit) 48, a ROM (read only memory) 50, a RAM (random access memory) 52, and an I/O (input-and-output) port, not shown. The CPU 48 processes signals according to the control programs pre-stored in the ROM 50, while utilizing the temporary-storage function of the RAM 52, and the CPU 48 outputs, from the I/O port, drive signals to the respective air pumps 36 and respective pressure control valves 26 of the four pulse-wave-detect consoles 24, so as to control the respective operations of those elements 36, 26 and thereby changes the respective pressures in the cuffs 18L, 18R, 20L, 20R. The CPU 48 controls the respective pressures of the cuffs 18L, 18R, 20L, 20R, so as to measure, according to an oscillometric method, respective blood-pressure values of the left ankle 12L, the right ankle 12R, the left upper arm 14L, and the right upper arm 14R around which the cuffs 18L, 18R, 20L, 20R are wound, respectively. Based on the respective blood-pressure values of the left ankle 12L, the right ankle 12R, the left upper arm 14L, and the right upper arm 14R, the CPU 48 determines an inferior-and-superior-limb blood-pressure index (e.g., inferior-limb systolic blood pressure/superior-limb systolic blood pressure), ABI, that is to be used to diagnose arteriostenosis. Moreover, the CPU 48 processes the signals supplied to the control device 38 and controls a display device 54 to display respective waveforms of respective arterial pulse waves occurring to the left and right cuffs 18L, 18R, 20L, 20R that are kept at respective pressures that would be lower than a diastolic blood pressure of the patient, such that those waveforms are apart from each other. Simultaneously, the CPU 48 controls the display device 54 to display those waveforms such that those waveforms are superimposed on each other. Furthermore, the CPU 48 judges whether a degree of sharpness determined based on each of those waveforms is greater than a reference value, and thereby makes a judgment about arteriostenosis of a portion located upstream of a portion where each one of the four cuffs 18L, 18R, 20L, 20R is worn, so as to control the display device 54 to display the judgments made and an arteriostenotic portion identified based on the judgments.

Figure 2:
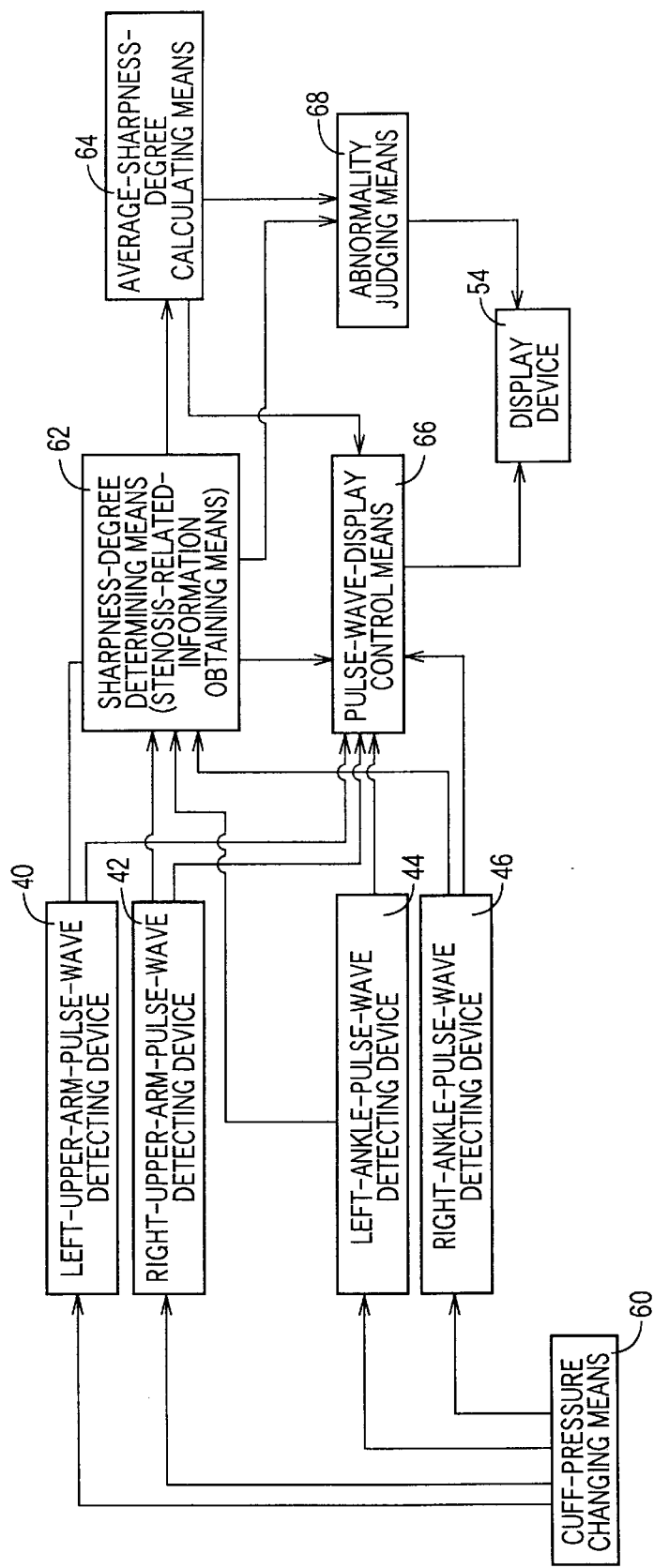
FIG. 2 is a diagrammatic view for explaining essential control functions of a CPU (central processing unit) of a control device, shown in FIG. 1.

FIG. 2 is a diagrammatic view for explaining essential control functions of the CPU 48. A cuff-pressure changing means 60 controls the respective air pumps 36a, 36b, 36c, 36d and respective pressure control valves 26a, 26b, 26c, 26d of the four pulse-wave detecting devices 40, 42, 44, 46, so as to control the respective cuff pressures $PC_a$, $PC_b$, $PC_c$, $PC_d$ to respective predetermined pulse-wave detecting pressures. The pulse-wave detecting pressures are predetermined at respective pressures which are lower than respective diastolic blood pressures of the respective portions where the cuffs 18, 20 are worn and which assure that the respective pulse-wave signals SM extracted by the respective pulse-wave filter circuits 32 have a sufficiently great magnitude, for example, are predetermined at 50 mmHg.

Figure 3:
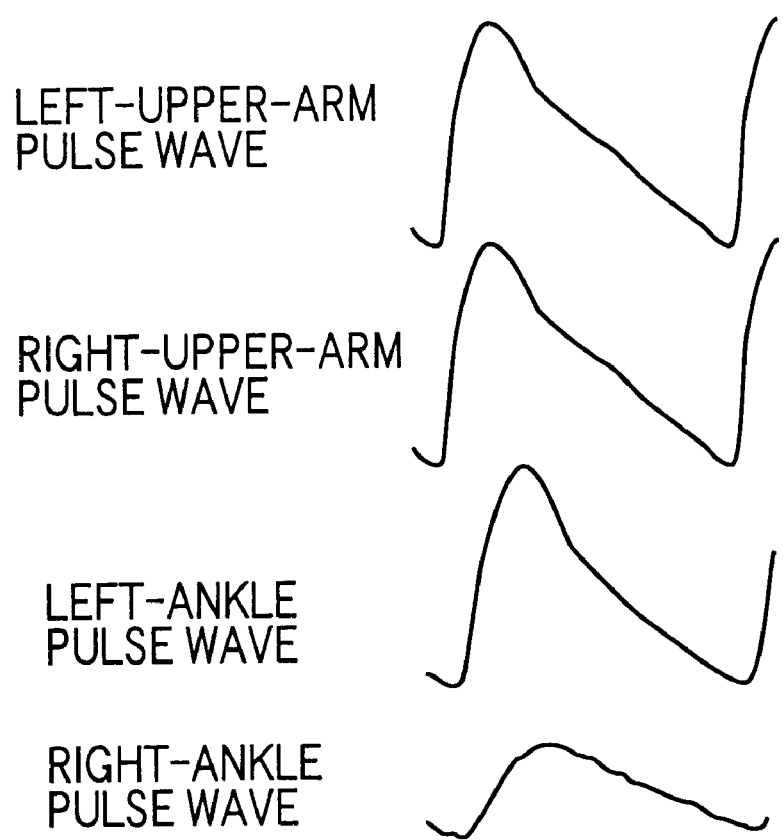
FIG. 3 is a graph showing respective shapes or forms of respective pulse waves detected by respective pulse-wave detecting devices which are worn on left and right superior limbs and left and right inferior limbs of a living subject.

The left-upper-arm pulse-wave detecting device 40, the right-upper-arm pulse-wave detecting device 42, the left-ankle pulse-wave detecting device 44, and the right-ankle pulse-wave detecting device 46 detect, in the state in which the cuff-pressure changing means 60 maintains the respective pressures $PC_a$, $PC_b$, $PC_c$, $PC_d$ of the respective cuffs 18L, 18R, 20L, 20R at the respective pulse-wave detecting pressures, the left-upper-arm pulse wave, the right-upper-arm pulse wave, the left-ankle pulse wave, and the right-ankle pulse wave, respectively, that are respective arterial pulse waves produced in synchronism with one another, and with heartbeats of the subject, from the respective arteries of the left upper arm 14L, the right upper arm 14R, the left ankle 12L, and the right ankle 12R. The CPU 48 stores the thus detected pulse waves in the RAM 52 functioning as a memory device. FIG. 3 shows respective examples of the left-upper-arm pulse wave $WB_L$, the right-upper-arm pulse wave $WB_R$, the left-ankle pulse wave $WA_L$, and the right-ankle pulse wave $WA_R$. The left-upper-arm, right-upper-arm, and left-ankle pulse waves $WB_L$, $WB_R$, $WA_L$ show normal waveforms, but the right-ankle pulse wave $WA_R$ shows an abnormal waveform, i.e., a typical waveform indicating arteriostenosis.

A sharpness-degree determining means 62 determines a degree of sharpness of each of successive heartbeat-synchronous pulses of each of the respective pulse waves detected by the four pulse-wave detecting devices 40, 42, 44, 46 in the state in which the respective cuff pressures $PC_a$, $PC_b$, $PC_c$, $PC_d$ are maintained at the respective pulse-wave detecting pressures by the cuff-pressure changing means 60. A degree of sharpness of a pulse wave corresponds to a degree of upward projection of the pulse wave. The sharpness degree may be expressed as a normalized pulse area VR (=S/(W×H)) which is obtained by dividing a pulse area S calculated by summarizing one heartbeat-synchronous pulse of, e.g., an upper-arm pulse wave WB shown in FIG. 4, over a pulse period W, by a product (W×H) of a height H of a peak point b and the pulse period W; a normalized value of a first area S1 calculated by summarizing a first portion from a rising point a to the peak point b; a normalized value of a second area S2 calculated by summarizing a second portion following the peak point b; or a normalized value I/W obtained by dividing, by the pulse period W, a width I of one heartbeat-synchronous pulse at a height equal to two thirds, H×(⅔), of the peak-point height H. The normalized pulse area VR may be expressed as a parameter % MAP (=100× G/H) that is a percentage of a height G of a center of gravity of the pulse area S relative to the peak-point height H, i.e., pulse pressure. If the patient has arteriostenosis in the portion located upstream of the portion where each one of the cuffs 18, 20 is worn, the degree of upward projection of heartbeat-synchronous pulse of the pulse wave detected by the each cuff 18, 20 lowers, and accordingly the parameter VR or % MAP increases. Thus, the sharpness degree functions as stenosis-related information, more specifically, waveform-characteristic information that changes in relation with arteriostenosis; and the sharpness-degree determining means 62 functions as a stenosis-related-information obtaining means. Respective sharpness degrees determined for the first and second pulse waves selected from the left-upper-arm pulse wave $WB_L$, the right-upper-arm pulse wave $WB_R$, the left-ankle pulse wave $WA_L$, and the right-ankle pulse wave $WA_R$, function as first stenosis-related information and second stenosis-related information, respectively.

An average-sharpness-degree calculating means 64 calculates an average of the respective sharpness degrees of the successive heartbeat-synchronous pulses of the left-upper-arm pulse wave $WB_L$, determined by the sharpness-degree determining means 62. Similarly, the average-sharpness-degree calculating means 64 calculates an average of the respective sharpness degrees of successive pulses of the right-upper-arm pulse wave $WB_R$, an average of the respective sharpness degrees of successive pulses of the left-ankle pulse wave $WA_L$, and an average of the respective sharpness degrees of successive pulses of the right-ankle pulse wave $WA_R$.

A pulse-wave-display control means 66 calculates a comparison value by comparing each of respective sharpness degrees of respective heartbeat-synchronous pulses of the left-upper-arm pulse wave $WB_L$, determined by the sharpness-degree determining means 62, with the average sharpness degree of the left-upper-arm pulse wave $WB_L$, calculated by the average-sharpness-degree calculating means 64, and, if the thus calculated comparison value falls within a predetermined range, the display control means 66 operates the display device 54 to display a waveform of the corresponding pulse of the left-upper-arm pulse wave $WB_L$. Here, a comparison value indicates a degree of difference between each sharpness degree and an average sharpness degree, and may be a difference itself between the two degrees, or a ratio of one of the two degrees to the other. The fact that a comparison value falls within the predetermined range means that its corresponding sharpness degree is around the average sharpness degree. Therefore, the display device 54 displays only a waveform of a heartbeat-synchronous pulse of the left-upper-arm pulse wave $WB_L$ that is less influenced or deformed by incidental noise such as arrhythmia or physical motion of the patient. Similarly, regarding each one of the right-upper-arm pulse wave $WB_R$, the left-ankle pulse wave $WA_L$, and the right-ankle pulse wave $WA_R$, the display control means 66 calculates a comparison value in the same manner as described above and, if the thus calculated comparison value falls within the predetermined range, operates the display device 54 to display a waveform of a heartbeat-synchronous pulse of the each pulse wave $WB_R$, $WA_L$, $WA_R$, as shown in FIG. 3.

An abnormality judging means 68 judges, based on each of the sharpness degrees of the left-upper-arm pulse wave $WB_L$ determined by the sharpness-degree determining means 62, whether an "upstream" artery of a portion located upstream of the portion where the left upper-arm cuff 20L is worn has stenosis or not. The sharpness degree increases as the degree of stenosis of the upstream artery increases. Therefore, if each sharpness degree determined from the left-upper-arm pulse wave $WB_L$ exceeds an upper limit of a predetermined normal range, then the abnormality judging means 68 judges that the artery located upstream of the left upper-arm cuff 20L has stenosis. Similarly, regarding each of the right-upper-arm pulse wave $WB_R$, the left-ankle pulse wave $WA_L$, and the right-ankle pulse wave $WA_R$, the abnormality judging means 68 judges, based on each of the sharpness degrees of the each pulse wave $WB_R$, $WA_L$, $WA_R$, determined by the sharpness-degree determining means 62, whether an "upstream" artery of a portion located upstream of the portion where the corresponding cuff 20R, 18L, 18R is worn has stenosis or not. Here, it is preferred that the judging means 68 use only the sharpness degrees determined for the heartbeat-synchronous pulses whose waveforms are displayed on the display device 54 by the pulse-wave-display control means 66, that is, only the sharpness degrees corresponding to the comparison values each falling within the predetermined range.

In addition, the abnormality judging means 68 identifies an arteriostenotic portion, based on the thus made four judgments about whether the respective arteries of the respective portions located upstream of the respective portions where the four cuff 20L, 20R, 18L, 18R are worn have stenosis or not, and a predetermined relationship between four judgments and arteriostenotic portion, pre-stored in the ROM 52, and operates the display device 54 to display the thus identified arteriostenotic portion of the patient, for example, in such a manner that one of symbols "A" through "F" that corresponds to the arteriostenotic portion is lit.

Figure 5:
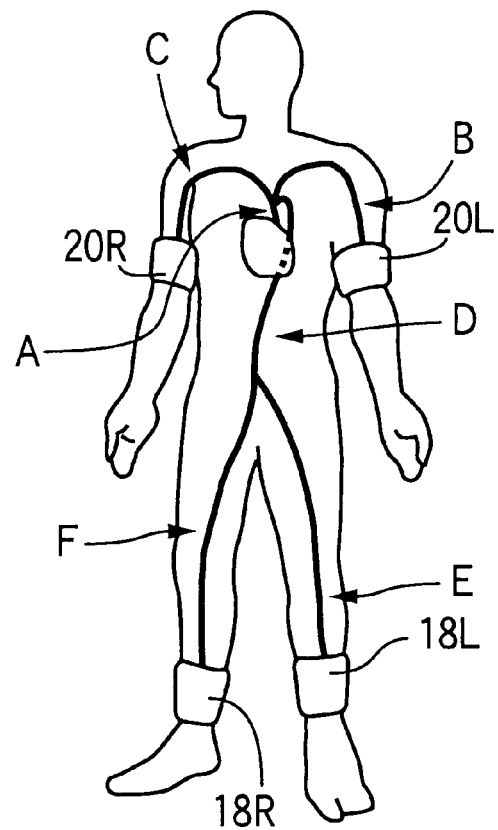
FIG. 5 is a view for explaining arteries of the subject that are displayed on a display device, shown in FIG. 1.

FIG. 6 shows a table representing the pre-stored relationship between four judgments and arteriostenotic portion. In the following description of the table shown in FIG. 6, it is assumed, for easier understanding purposes only, that the four pulse-wave detecting devices 40, 42, 44, 46 function as a third, a fourth, the first, and the second pulse-wave detecting device, respectively, and that the respective arteries of the respective portions located upstream of the respective portions where the four cuff 20L, 20R, 18L, 18R are worn are a third, a fourth, a first, and a second artery of the patient, respectively. However, since the first and second pulse-wave detecting devices can be arbitrarily selected from the four pulse-wave detecting devices 40, 42, 44, 46, as described above, the first and second arteries can also be arbitrarily selected from the four arteries located upstream of the four cuff 20L, 20R, 18L, 18R. In addition, it is assumed, as shown in FIG. 5, that an artery between the heart and a junction of the third and fourth arteries (hereinafter, referred to as the first junction) is an artery A; an artery between the first junction and the portion where the left-upper-arm cuff 20L is worn is an artery B; an artery between the first junction and the portion where the right-upper-arm cuff 20R is worn is an artery C; an artery between the first junction and a junction of the first and second arteries (hereinafter, referred to as the second junction) is an artery D; an artery between the second junction and the portion where the left-ankle cuff 18L is worn is an artery E; and an artery between the second junction and the portion where the right-ankle cuff 18R is worn is an artery F.

In the table shown in FIG. 6, symbol "O" indicates absence of stenosis and symbol "X" indicates presence of stenosis. The relationship shown in the table of FIG. 6 will be described in more detail below. For example, the third line of the table shows that only the first artery has stenosis and, in this case, the abnormality judging means 68 judges that a portion of the first artery that is not common to the other arteries, i.e., the artery E is a stenotic portion. The sixth line of the table shows that the first and second arteries have stenosis and the third and fourth arteries do not have stenosis and, in this case, the abnormality judging means 68 judges that a portion that is common to the first and second arteries and is not common to the third and fourth arteries, i.e., the artery D is a stenotic portion. The last line of the table shows that all the arteries have stenosis and, in this case, the abnormality judging means 68 judges that a portion that is common to all the arteries, i.e., the artery A is a stenotic portion (e.g., aortic stenosis). Here, it is noted that the table of FIG. 6 is prepared on the assumption that a living subject has a single stenotic portion.

Figure 4:
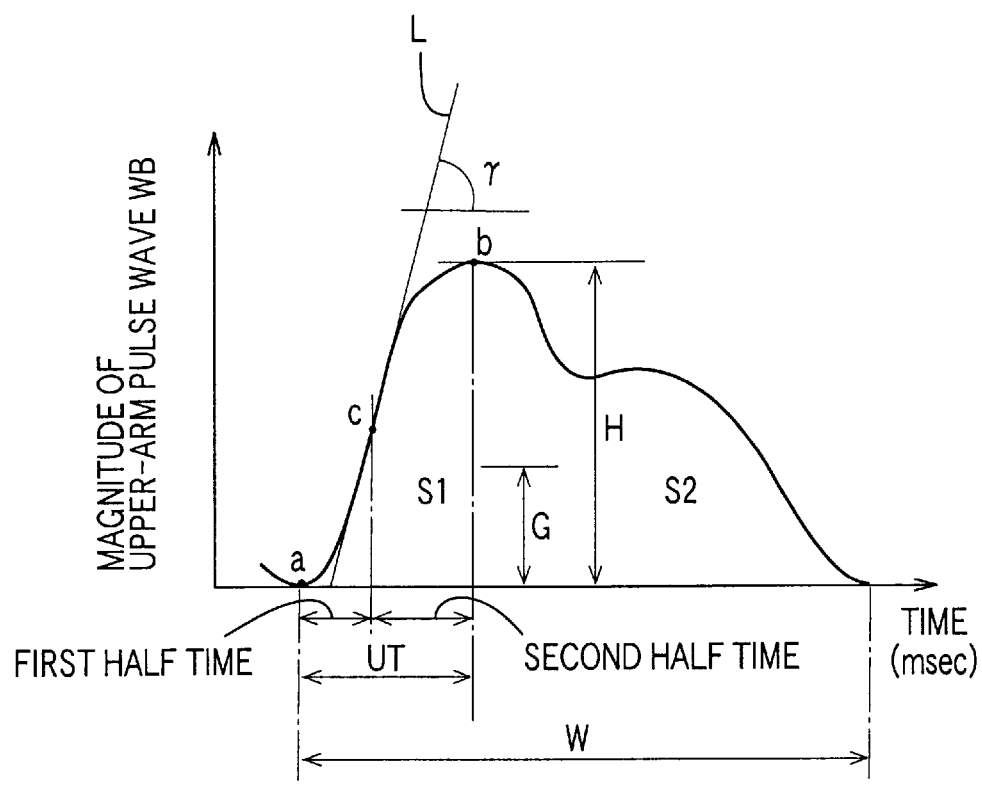
FIG. 4 is a graph for explaining a normalized pulse-wave area VR as a degree of sharpness that is characteristic of the pulse wave detected by each of the pulse-wave detecting devices.
Figure 7:
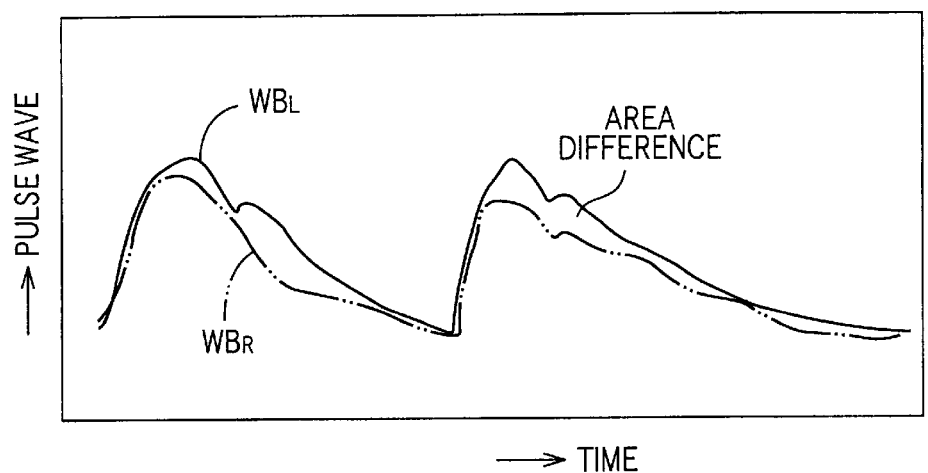
FIG. 7 is a graph showing two pulse waves that are detected from left and right limbs of the subject, and are superposed on each other by a pulse-wave-display control means, shown in FIG. 2.

The pulse-wave-display control means 66 operates the display device 54 to display the two noise-free pulse waves produced in synchronism with each other from the left and right portions of the subject that are located at respective positions symmetrical with each other with respect to a median line of the subject, for example, the left and right upper-arm pulse waves $WB_L$, $WB_R$, or the left and right ankle pulse waves $WA_L$, $WA_R$, such that the two pulse waves are superposed on each other in a common two-dimensional coordinate system defined by a first axis indicative of time and a second axis indicative of magnitude of pulse wave, as shown in FIG. 7. In FIG. 7, the left-upper-arm pulse wave $WB_L$ is indicated at solid line, and the right-upper-arm pulse wave $WB_R$ is indicated at two-dot chain line. The display device 54 displays those two waveforms such that respective minimal points or respective rising points of the two waveforms coincide with each other. A rising point of a waveform is defined as a point which is located in the vicinity of a minimal point and has a magnitude equal to from one fifth to one tenth of an amplitude of the waveform, i.e., a magnitude of a peak point of the waveform. In FIG. 4, a minimal point is indicated at point a; a peak point is indicated at point b; and an amplitude of a waveform is indicated at height H. Alternatively, a rising point is defined as a point where a line L tangential to a point c having a maximal slope intersects a base line passing the minimal point a. In addition, the display device 54 may display those two waveforms in a normalized manner, i.e., in such a manner that respective amplitudes of the two waveforms are equal to each other. However, since those two waveforms are synchronous waveforms that have simultaneously occurred in synchronism with a heartbeat of the subject, they are not needed to be normalized with respect to wavelength.

In addition, the abnormality judging means 68 includes an area-difference determining means for determining a difference of respective areas of the two waveforms shown in FIG. 7, i.e., a sum of respective differences between respective data points of one of the two waveforms and respective data points of the other waveform; and a judging means for judging whether the area difference determined by the area-difference determining means is greater than a pre-set reference value. The pulse-wave-display control means 66 operates the display device 54 to display the area difference, determined by the area-difference determining means, in a digital value such as numerals, or an analog value such as a bar graph. When the judging means judges that the subject has an abnormality, e.g., arteriostenosis, the control means 66 operates the display device 54 to display a message indicating the abnormality.

Figure 8:
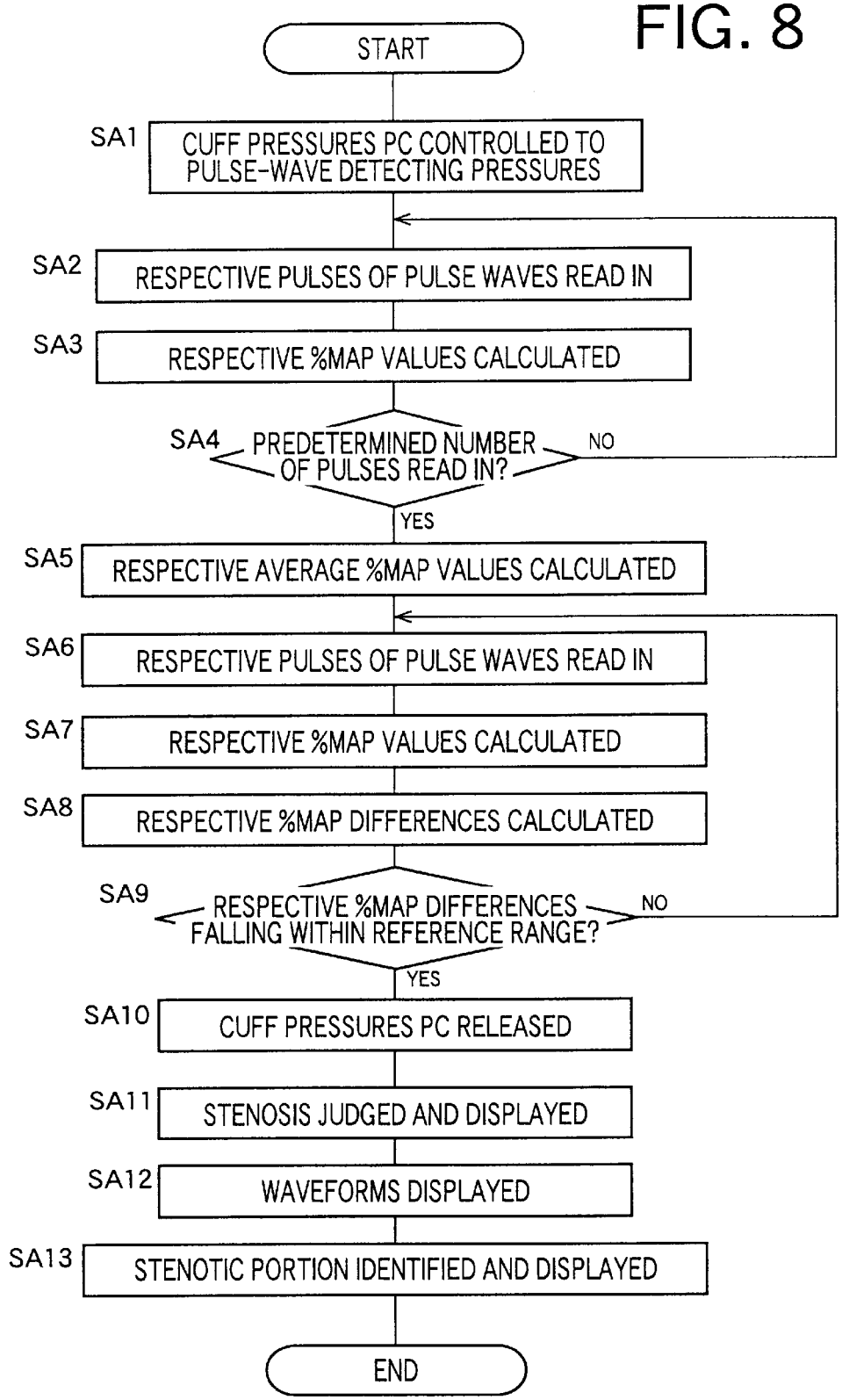
FIG. 8 is a flow chart representing the essential control functions of the CPU shown in FIG. 1.

FIG. 8 is a flow chart representing the essential control functions of the CPU 48, shown in FIG. 2. First, at Step SA1 of FIG. 8 (hereinafter, the terms "Step(s)" are omitted) corresponding to the cuff-pressure changing means 60, the CPU controls the air pumps 36a, 36b, 36c, 36d and the pressure control valves 26a, 26b, 26c, 26d to change and maintain the cuff pressures $PC_a$, $PC_b$, $PC_c$, $PC_d$ to and at the above-described respective pulse-wave detecting pressures.

Then, at SA2, the CPU reads in one heartbeat-synchronous pulse of each of the respective pulse waves supplied from the four pulse-wave detecting devices 40, 42, 44, 46. Then, the control goes to SA3 corresponding to the sharpness-degree determining means 62. At SA3, the CPU determines a % MAP value of each of the respective heartbeat-synchronous pulses of the four pulse waves, read in at SA2. Then, the control goes to SA4 where the CPU judges whether the CPU has read in, at SA2, a predetermined number of (e.g., ten) heartbeat-synchronous pulses of each of the four pulse waves. If a negative judgment is made at SA4, the control goes back to SA2.

Meanwhile, if a positive judgment is made at SA4, then the control goes to SA5 corresponding to the average-sharpness-degree calculating means 64. At SA5, the CPU calculates an average of the respective % MAP values of the predetermined number of pulses of each of the four pulse waves, i.e., calculates respective average % MAP values of the four pulse waves. Then, the control goes to SA6 where the CPU again reads in one heartbeat-synchronous pulse of each of the respective pulse waves supplied from the four pulse-wave detecting devices 40, 42, 44, 46. Then, the control goes to SA7 corresponding to the sharpness-degree determining means 62. At SA7, the CPU determines a third % MAP value (i.e., third stenosis-related information) of the heartbeat-synchronous pulse of the left-upper-arm pulse wave $WB_L$, a fourth % MAP value (i.e., fourth stenosis-related information) of the heartbeat-synchronous pulse of the right-upper-arm pulse wave $WB_R$, a first % MAP value (i.e., first stenosis-related information) of the heartbeat-synchronous pulse of the left-ankle pulse wave $WA_L$, and a second % MAP value (i.e., second stenosis-related information) of the heartbeat-synchronous pulse of the right-ankle pulse wave $WA_R$.

Then, at SA8, the CPU calculates respective % MAP differences by subtracting, from the respective % MAP values of the four pulse waves, determined at SA7, the respective average % MAP values of the four pulse waves, calculated at SA5. Subsequently, the control goes to SA9 where the CPU judges whether each of the four % MAP differences, calculated at SA8, falls within a predetermined reference range whose middle value is equal to zero and which is considerably narrow. A positive judgment made at SA9 means that each of the % MAP values, determined at SA7, and a corresponding one of the average % MAP values, calculated at SA5, are close to each other, and additionally means that a shape of a corresponding one of the four heartbeat-synchronous pulses, read in at SA6, has little deformation and accordingly is suitable for use in making a diagnosis about arteriotenosis. Therefore, if a positive judgment is made at SA9, the control goes to SA10 and the following steps, without read in additional pulses of the four pulse waves. On the other hand, if a negative judgment is made at SA9, the control goes back to SA6.

At SA10, the CPU stops the air pumps 36a, 36b, 36c, 36d and controls the pressure control valves 26a, 26b, 26c, 26d to decrease the cuff pressures $PC_a$, $PC_b$, $PC_c$, $PC_d$ each to an atmospheric pressure. In the present flow chart, SA1 and SA10 corresponding to the cuff-pressure changing means 60.

Then, at SA11 corresponding to the abnormality judging means 68 and the pulse-wave-display control means 66, the CPU judges, based on the % MAP value of each one of the first to fourth pulse waves, determined at SA7, whether a corresponding one of the first to fourth arteries has abnormality (i.e., stenosis). More specifically described, if the % MAP value of each one of the first to fourth pulse waves, determined at SA7, falls within a corresponding one of respective normal ranges predetermined for the four pulse waves, the CPU judges that one of the first to fourth arteries that corresponds to the each one pulse wave does not have stenosis; and if not, the CPU judges that the one artery has stenosis. Each one of the first to fourth pulse waves is detected from the downstream end of a corresponding one of the first to fourth arteries. In addition, the CPU operates the display device 54 to display the results of those judgments. In addition, at SA11, the CPU judges whether a difference of respective areas of the two pulse waves, e.g., the left and right upper-arm pulse waves $WB_L$, $WB_R$, that are detected from the left and right portions of the subject being in a stable state and are superposed on each other such that the respective rising points of the two pulse waves coincide with each other, is greater than a pre-set reference value and, if a positive judgment is made, the CPU judges that the subject has arteriostenosis, and operates the display device 54 to display the result of judgment.

Then, at SA12 corresponding to the pulse-wave-display control means 66, the CPU operates the display device 54 to display respective waveforms of the two pulse waves, e.g., the left and right upper-arm pulse waves $WB_L$, $WB_R$, that are detected from the left and right portions of the subject, such that those two waveforms are superposed on each other, more specifically described, the respective rising points or respective minimal points of the two waveforms coincide with each other. At SA12, preferably, the CPU operates the display device 54 to display the two waveforms such that respective amplitudes of the two waveforms are equal to each other. In addition, at SA12, the CPU identifies an arteriostenotic portion of the subject and operates the display device 54 to display the thus-identified arteriostenotic portion of the subject. For example, if the right upper-arm pulse wave $WB_R$ is smaller than the left upper-arm pulse wave $WB_L$ and the area difference is greater than the reference value, then the CPU operates the display device 54 to display a message that the right brachial artery of the subject may have arteriostenosis. Moreover, at SA12, the CPU operates the display device 54 to display the respective waveforms of the four pulse waves, read in at SA6, that correspond to the respective % MAP differences for which the positive judgment had been made at SA9. FIG. 3 shows respective examples of the respective pulses of the four pulse waves, displayed at SA12. From FIG. 3, it can be understood that a sharpness degree of the pulse of the right-ankle pulse wave $WA_R$ only is low and, from this fact, it can be judged by a medical person that the right inferior limb has stenosis.

Subsequently, at SA13, the CPU identifies a stenotic portion of the patient based on the presence or absence of stenosis in each of the first to fourth arteries, judged at SA11, and the relationship shown in the table shown in FIG. 6, and operates the display device 54 to display the identified stenotic portion.

Thus, in the illustrated embodiment, the pulse-wave-display control means 66 (SA12) operates the display device 54 to display the plurality of pulse waves produced in synchronism with each other, detected by the plurality of pulse-wave detecting devices 40, 42, 44, 46, and stored in the RAM (i.e., the memory device) 52, such that those pulse waves are superposed on each other. Thus, each of those waveforms can be easily compared with the other waveform or waveforms, so that a person can more easily and accurately identify even a small change or difference of any one of those waveforms. That is, the accuracy of inspection of the waveform of arterial pulse wave can be improved.

In addition, in the illustrated embodiment, the pulse-wave-display control means 66 (SA12) operates the display device 54 to display the plurality of pulse waves synchronous with each other, such that the respective minimal points thereof coincide with each other. Thus, a person can more easily and accurately identify even a small change of any one of those arterial waveforms.

Moreover, in the illustrated embodiment, the pulse-wave-display control means 66 (SA12) operates the display device 54 to display the plurality of pulse waves synchronous with each other, such that the respective rising points thereof coincide with each other. Thus, a person can more easily and accurately identify even a small change of any one of those arterial waveforms.

In addition, in the illustrated embodiment, the pulse-wave-display control means 66 (SA12) operates the display device 54 to display the plurality of pulse waves synchronous with each other, such that the respective amplitudes thereof are equal to each other. Thus, a person can more easily and accurately identify even a small change of any one of those arterial waveforms.

Also, in the illustrated embodiment, the area-difference determining means determines the difference of the respective areas of the two pulse waves that are displayed on the display device 54 by the pulse-wave-display control means 66 (SA12), such that the two pulse waves are superposed on each other. The pulse-wave-display control means 66 (SA11) operates the display device 54 to display the area difference determined by the area-difference determining means. Thus, the difference of the two pulse waves are quantitatively recognized. In addition, a slow or overall change of a waveform that cannot be easily recognized in a conventional manner can be easily identified or recognized according to the present invention.

Also, in the illustrated embodiment, the plurality of pulse-wave detecting devices 40, 42, 44, 46 detect the respective pulse waves produced from the respective arteries of the left and right portions of the subject that are located at the respective positions symmetrical with each other with respect to the median line of the subject, and pulse-wave-display control means 66 (SA11) operates the display device 54 to display the two pulse waves detected from the left and right portions, such that those pulse waves are superposed on each other. Thus, a person can easily compare the two pulse waves with each other. Therefore, a person can more easily and accurately identify even a small change of either one of the two waveforms. That is, the accuracy of inspection of the waveform of each arterial pulse wave can be improved. Since the two waveforms should be basically identical with each other, the change of each of the waveforms can be more easily identified.

While the present invention has been described in its preferred embodiment by reference to the drawings, the present invention may be otherwise embodied.

For example, in the illustrated embodiment, the four pulse-wave detecting devices 40, 42, 44, 46 are employed. However, it is possible to employ a different number of pulse-wave detecting devices; such as one or two pulse-wave detecting devices only. In addition, the pulse-wave detecting devices 40, 42, 44, 46 employ the respective cuffs 18L, 18R, 20L, 20R to detect the respective pulse waves. However, those devices may be replaced with pressure-pulse-wave detecting devices which employs respective pressure sensors that are pressed against respective arteries of a living subject to detect respective pulse waves produced from the respective arteries. Moreover, it is possible to employ, as one or more of the pulse-wave detecting devices, a photoelectric-pulse-wave detecting probe for use in oxygen-saturation measurement; a pressure-pulse-wave sensor which is pressed against a prescribed artery such as a radial artery via skin to detect a pressure pulse wave; an impedance-pulse-wave sensor which detects, through electrodes, impedance of, e.g., an arm or a finger; or a photoelectric-pulse-wave sensor which is worn on, e.g., an end portion of a finger to detect pulsation.

Each of the pulse-wave detecting devices may be worn on a portion of a living subject other than an upper arm or an ankle. For example, it is possible to employ a pulse-wave detecting device adapted to be worn on a foot articulation in place of an ankle. In addition, it is possible to employ a pulse-wave detecting device which includes a cuff adapted to be worn on a femoral portion and detects a pulse wave from the cuff. In the case where respective pulse waves are detected from a femoral portion and an ankle, it is possible to make a judgment about arteriostenosis of an intermediate portion between the femoral portion and the ankle.

While the present invention has been described in detail in its preferred embodiment by reference to the drawings, it is to be understood that the present invention is by no means limited to the details of the described embodiment and may be embodied with other changes and improvements that may occur to a person skilled in the art without departing from the spirit and scope of the invention defined in the appended claims.

What is claimed is:

1. An arterial-pulse-wave detecting apparatus, comprising:
   a plurality of pulse-wave detecting devices which are adapted to be worn on a plurality of portions of a living subject, respectively, and detect respective pulse waves that are produced in synchronism with each other from respective arteries of the plurality of portions of the subject;
   a memory device which stores the respective pulse waves produced in synchronism with each other and detected by the plurality of pulse-wave detecting devices; and
   a pulse-wave-display control means for controlling a display device to display the respective pulse waves produced in synchronism with each other and stored by the memory device, such that the respective pulse waves are superposed on each other.

2. An apparatus according to claim 1, wherein the pulse-wave-display control means controls the display device to display the respective pulse waves produced in synchronism with each other, such that respective minimal points of the respective pulse waves coincide with each other.

3. An apparatus according to claim 1, wherein the pulse-wave-display control means controls the display device to display the respective pulse waves produced in synchronism with each other, such that respective rising points of the respective pulse waves coincide with each other.

4. An apparatus according to claim 1, wherein the pulse-wave-display control means controls the display device to display the respective pulse waves produced in synchronism with each other, such that respective amplitudes of the respective pulse waves are equal to each other.

5. An apparatus according to claim 1, further comprising an area-difference determining means for determining a difference between respective areas of the respective pulse waves displayed on the display device by the pulse-wave-display control means such that the respective pulse waves are superposed on each other, wherein the pulse-wave-display control means controls the display device to display the difference determined by the area-difference determining means.

6. An apparatus according to claim 5, further comprising a judging means for judging, based on the area difference determined by the area-difference determining means, whether the subject is suspected to have arteriostenosis, wherein the pulse-wave-display control means controls, when the judging means makes a positive judgment, the display device to display information indicating that the subject is suspected to have arteriostenosis.

7. An apparatus according to claim 1, wherein the plurality of pulse-wave detecting devices comprise two pulse-wave-detecting devices which include respective portions adapted to be worn on left and right portions of the subject, respectively, that are located at respective positions symmetrical with each other with respect to a median line of the subject, and detect the respective pulse waves produced from the respective arteries of the left and right portions of the subject, and wherein the pulse-wave-display control means controls the display device to display the respective pulse waves produced from the respective arteries of the left and right portions of the subject, such that the respective pulse waves are superposed on each other.

8. An apparatus according to claim 1, further comprising the display device which displays the respective pulse waves produced in synchronism with each other and stored by the memory device, such that the respective pulse waves are superposed on each other in a common two-dimensional coordinate system which is defined by a first axis indicative of time and a second axis indicative of pulse-wave magnitude.

9. An apparatus according to claim 1, further comprising:
   a stenosis-related-information obtaining means for obtaining, based on a shape of the pulse wave detected by each of the plurality of pulse-wave detecting devices, stenosis-related information that changes in relation with stenosis of an artery of an upstream portion of the subject that is located upstream of a corresponding one of the plurality of portions of the subject in a direction in which blood flows in the artery; and
   a stenosis judging means for making, based on the stenosis-related information obtained by the stenosis-related-information obtaining means, a judgment about the stenosis of the artery of the upstream portion of the subject.

* * * * *